United States Patent
Huang et al.

(10) Patent No.: US 8,116,407 B2
(45) Date of Patent: *Feb. 14, 2012

(54) DATA RECOVERY SYSTEM AND METHOD THEREOF

(75) Inventors: Chao-ming Huang, Hsin-Tien (TW); Meng-ta Yang, Jhunan Township (TW)

(73) Assignee: Mediatek Inc., Hsin-Chu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 12/857,492

(22) Filed: Aug. 16, 2010

(65) Prior Publication Data

US 2010/0310020 A1   Dec. 9, 2010

Related U.S. Application Data

(63) Continuation of application No. 11/696,000, filed on Apr. 3, 2007, now Pat. No. 7,801,251.

(51) Int. Cl.
   *H04L 27/00* (2006.01)
(52) U.S. Cl. .................................................. 375/326
(58) Field of Classification Search ................. 375/326, 375/341, 316; 714/795; 341/94; 369/47.24, 369/59.22

See application file for complete search history.

(56) References Cited

U.S. PATENT DOCUMENTS

| | | | |
|---|---|---|---|
| 7,321,531 B2 | 1/2008 | Park et al. | |
| 7,477,709 B2 | 1/2009 | Park et al. | |
| 2006/0123328 A1 | 6/2006 | Tonami et al. | |
| 2008/0108310 A1* | 5/2008 | Tong et al. | ...................... 455/69 |

FOREIGN PATENT DOCUMENTS

EP   1496512 A1   1/2005

* cited by examiner

*Primary Examiner* — Khai Tran

(57) ABSTRACT

A data recovery system and method is disclosed. Said data recovery system comprises a maximum-likelihood detector, a non-maximum likelihood detector, signal-length calculator, a determining unit and a selecting unit. The maximum-likelihood detector transforms a digital signal into a first binary signal. The non-maximum likelihood detector transforms the digital signal into a second binary signal. The signal-length calculator calculates a length of the first binary signal and a length of one previous to the first binary signal. The determining unit generates a selecting signal when the length of the first binary signal and the length of one previous to the first binary signal meet a criterion. The selecting unit coupled to the maximum-likelihood detector and the non-maximum likelihood detector, selectively outputs the first binary signal or the second binary signal based on the selecting signal.

14 Claims, 6 Drawing Sheets

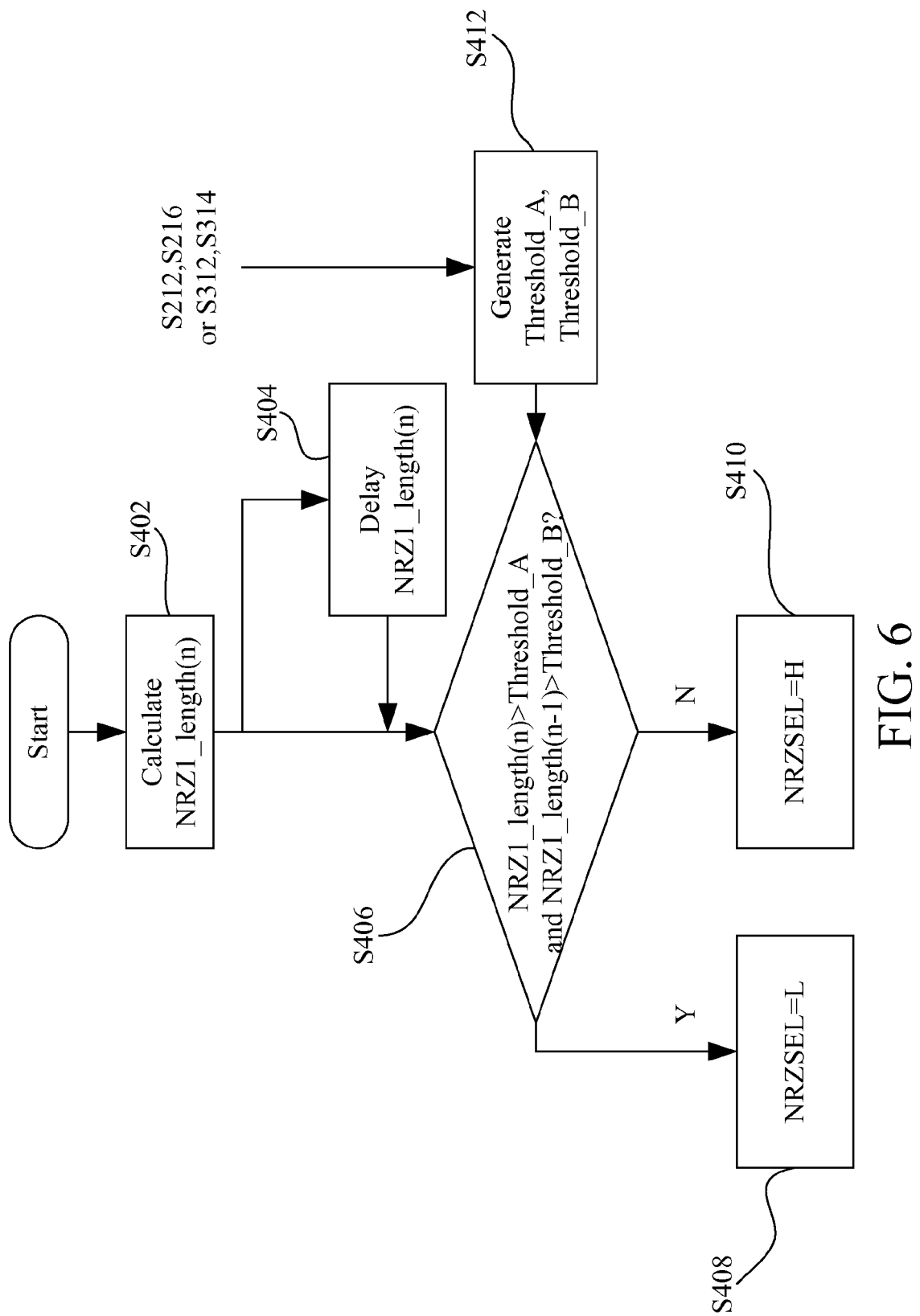

DATA RECOVERY SYSTEM AND METHOD THEREOF

CROSS REFERENCE TO RELATED APPLICATION

This is a Continuation Application of U.S. application Ser. No. 11/696,000, filed on Apr. 3, 2007 now U.S. Pat. No. 7,801,251, which is incorporated herein by reference in its entirety.

BACKGROUND OF THE INVENTION

1. Field of the Invention

The present invention relates to a data recovery system and method thereof, more specifically, to a data recovery system and method thereof capable of outputting corresponding binary signals in response to various patterns.

2. Description of the Related Art

When an optical disc drive reads a high-density optical disc such as a Blue-ray Disc (BD) and a High Density-Digital Versatile Disk (HD-DVD), a maximum-likelihood (ML) detector, for example a Viterbi decoder, is widely used for overcoming an inter-symbol interference (ISI) (interference between reproduced signals corresponding to bits recorded adjacent to each other) for data recovery. For a low-density optical disc, a non-maximum-likelihood detector, e.g. a data slicer, is commonly used on account of non-critical ISI. As for a medium-density disc, e.g. a Digital Versatile Disk (DVD), the non-maximum likelihood detector was mostly utilized in the past. However, in recent years, for raising capability of data recovery for a recordable/rewritable DVD, the maximum likelihood detector is applied in the optical disc drive.

Theoretically, maximum likelihood detector is a widely used technique for increasing the capability of data recovery. In fact, due to present day advancement in the recordable/rewritable DVD and a rapid advancement of recording/re-writing speed for the optical disc drive, reproducing signals corresponding to bits recorded adjacent to each other on a disc may realize some special patterns not complying with channel responses of the maximum likelihood detector. Such special patterns reduce capability of data recovery and increase the data error rate for the maximum likelihood detector. However, such special patterns may result in better data recovery capability for the non-maximum likelihood detector. Despite re-designing the maximum likelihood detector, a solution to improve the capability of data recovery for reading such special patterns will inevitably lead to a complex maximum likelihood detector.

SUMMARY OF INVENTION

It is, therefore, a primary objective of the claimed invention to provide a data recovery system and method thereof capable of selectively switching the process of data recovery. That is, if a pattern tends to make the maximum likelihood detector to be erred, then switching the non-maximum likelihood detector to perform pattern transforming is necessary; conversely, if a pattern tends to make the maximum likelihood detector to be erred, then switching the maximum likelihood detector to perform pattern transforming. In this way, an existing problem using a single detector is solved.

According to the claimed invention, a data recovery system comprises a maximum likelihood detector, a non-maximum likelihood detector, a signal-length calculator, a determining unit, and a selecting unit. The maximum-likelihood detector is used for transforming a digital signal into a first binary signal. The non-maximum likelihood detector is used for transforming the digital signal into a second binary signal. The signal-length calculator is used for calculating a length of the first binary signal and a length of one previous to the first binary signal. The determining unit is used for generating a selecting signal when the length of the first binary signal and the length of one previous to the first binary signal meet a criterion. The selecting unit, coupled to the maximum likelihood detector and the non-maximum likelihood detector, is used for selectively outputting the first binary signal or the second binary signal based on the selecting signal.

In one aspect of the present invention, the maximum-likelihood detector is a Viterbi decoder and the non-maximum likelihood detector is a data slicer.

In another aspect of the present invention, data recovery system further comprises a timer, a first counter, a second counter, and a threshold generator. The timer is used for timing a predetermined time period. The first counter, in the predetermined time period, is used for counting a third counting value indicating an amount of the differences, when a logical level of the first binary signal and a logical level of the second binary signal are not identical when the first binary signal is in a rising edge. The second counter, in the predetermined time period, is used for counting a fourth counting value indicating an amount of the differences, when the logical level of the first binary signal and the logical level of the second binary signal are not identical when the first binary signal is in a falling edge. The threshold generator is used for adjusting the first predefined value and the second predefined value based on the third counting value and the fourth counting value when a sum of the third counting value and the fourth counting value is larger than a third predefined value, and when the third counting value do not equal to the fourth counting value.

In still another aspect of the present invention, the first binary and the second binary signals are selected from a group consisting of a non-return-to-zero (NRZ) signal and a non-return to zero inverted (NRZI) signal.

In still another aspect of the present invention, the criterion indicates the length of the first binary signal is larger than a first predefined value, and the length of the one previous to the first binary signal is larger than a second predefined value.

According to the claimed invention, a data recovery method comprises the steps of receiving a digital signal, transforming the digital signal into a first binary signal by using maximum-likelihood logic, transforming the digital signal into a second binary signal by using non-maximum likelihood logic, calculating a length of the first binary signal and a length of one previous to the first binary signal, generating the selecting signal when the length of the first binary signal and the length of one previous to the first binary signal meet a criterion, and selectively outputting the first binary signal or the second binary signal based on the selecting signal.

In one aspect of the present invention, the criterion indicates the length of the first binary signal is larger than a first predefined value, and the length of one previous to the first binary signal is larger than a second predefined value.

In another aspect of the present invention, the method further comprises step of counting a first counting value indicating an amount of the differences between the first binary signal at a first logical level and the second binary signal at a second logical level in a predetermined time period; counting a second counting value indicating an amount of the differences between the first binary signal at the second logical level and the second binary signal at the first logical level in the predetermined time period; and adjusting the first predefined value and the second predefined value based on the first counting value and the second counting value, when a sum of the first counting value and the second counting value is larger than a third predefined value, and when the first counting value does not equal to the second counting value.

In yet another aspect of the present invention, the method further comprises the steps of counting a third counting value indicating an amount of the differences, when a logical level of the first binary signal and a logical level of the second binary signal are not identical when the first binary signal is in a rising edge in a predetermined time period; counting a fourth counting value indicating an amount of the differences, when the logical level of the first binary signal and the logical level of the second binary signal are not identical when the first binary signal is in a falling edge in the predetermined time period; and adjusting the first predefined value and the second predefined value based on the third counting value and the fourth counting value, when a sum of the third counting value and the fourth counting value is larger than a third predefined value, and when the third counting value do not equal to the fourth counting value.

In still another aspect of the present invention, the first binary and the second binary signals are selected from a group consisting of a non-return-to-zero (NRZ) signal and a non-return to zero inverted (NRZI) signal.

It is an advantage of the present invention that the decision unit is used to calculate the difference between the first binary signal NRZ1 and the second binary signal NRZ2 in a predetermined time period, and then switching either the maximum likelihood detector (e.g. Viterbi decoder) or the non-maximum likelihood detector (e.g. data slicer) based on the calculation of the difference, and executing data recovery is performed. Consequently, properly switching the current maximum-likelihood detector and non-maximum-likelihood detector is a solution to improve data recovery efficiency, without designing a new complex maximum-likelihood detector.

These and other objectives of the present invention will no doubt become obvious to those of ordinary skill in the art after reading the following detailed description of the preferred embodiment, which is illustrated in the various figures and drawings.

DETAILED DESCRIPTION OF THE PREFERRED EMBODIMENT

Please refer to FIG. 1, which is a functional block diagram of a preferred embodiment of a data recovery system 40 according to the present invention. The data recovery system 40 can be applied in an optical drive 10. A pickup head 12 of the optical drive 10 emits light beam toward an optical disc 5, and produces analog reproduced signal based on reflective light beam from the optical disc 5. The analog reproduced signal is then fed into a pre-amplifier and a pre-equalizer 14 respectively, which are used for adjusting gain control to make magnitude of the analog reproduced signal complying with an input range of an analog to digital converter (A/D converter) 16, and for filtering out high-frequency noise and low-frequency jitter of the analog reproduced signal. Thereafter, the A/D converter 16 transforms the analog reproduced signal into digital reproduced signal.

Digital reproduced signal is then fed into a data recovery system 40 and a timing recovery unit 18 for recovering a channel bit clock (CBCLK) which is used for synchronization of digital reproduced signal. The clock signal of both the analog-to-digital converter 16 and the data recovery system 40 follows the channel bit clock (CBCLK).

In this preferred embodiment, the data recovery system 40 comprises a digital equalizer 22, a maximum likelihood detector (ML detector) 24, a non-maximum likelihood detector (non-ML detector) 26, a selecting unit 28, and a decision unit 30. The ML detector 24 may be a Viterbi decoder, and the non-ML detector 26 may be a data slicer. For simplicity reason, operation principles of either the Viterbi decoder or the data slicer is aware by the skilled person in this art, therefore, no further detail is described hereinafter. The ML detector 24 and the non-ML detector 26 respectively convert the digital equalized signal into a first binary signal and a second binary signal (hereinafter referred to as NRZ1 and NRZ2). It is noted that the ML detector 24 and the non-ML detector 26 employ respective algorithms to convert the identical digital equalized signal into two kinds of slightly different binary signals. In general, the binary signals are selected from a group consisting of non-return-to-zero (NRZ) signals and non-return-to-zero inverted (NRZI) signals. For clarity, non-return-to-zero signals are introduced in the following embodiments according to the present invention. The decision unit 30 detects differences between the first non-return-to-zero signal (NRZ1) generated by the ML detector 24, and the second non-return-to-zero signal (NRZ2) generated by the non-ML detector 26 in a predetermined time period. Also the decision unit 30 outputs a selecting signal NRZSEL to a selecting unit 28 in response to an amount of the detected differences. Finally, the selecting unit 28 selectively outputs the first non-return-to-zero signal NRZ1 from the ML detector 24 or the second non-return-to-zero signal NRZ2 from the non-ML detector 26 based on the selecting signal NRZSEL.

Please refer to FIGS. 2 and 3. FIG. 2 is a functional block diagram of a preferred embodiment of the decision unit 30 depicted in FIG. 1. FIG. 3 is a flowchart of a preferred embodiment method incorporating the decision unit 30 depicted in FIG. 2. The decision unit 30 comprises a first counter 301, a second counter 302, a calculating unit 304, a timer 306, and a comparator 308. First of all, the first counter 301, the second counter 302, and the timer 306 return to zero (as in Step S202) to get ready for counting an amount of differences between the first non-return-to-zero signal NRZ1 and the second non-return-to-zero signal NRZ2 in a predetermined time period. The timer 306 which can be implemented by a counter sequentially sums a counting value NRZCnt associated with a period cycle of the channel bit clock CBCLK (NRZCnt=NRZCnt+1, as in Step S204) until the counting value NRZcnt matches a predetermined value LEVEL_A (Step S206). As long as the counting value NRZcnt matches the predetermined value LEVEL_A, it indicates that the predetermined time period is up. In this preferred embodiment, the predetermined value LEVEL_A can be set to 4×8192 T, where T indicates the period cycle of the channel bit clock (CBCLK).

Prior to reaching the predetermined time period, a comparator 308 successively compares the first non-return-to-zero signal NRZ1 with the second non-return-to-zero signal NRZ2. In this embodiment, the comparator 308 detects whether the first non-return-to-zero signal NRZ1 is at high voltage level or not (Step S208); if it is, further determination of whether the first non-return-to-zero signal NRZ1 has the same voltage level as the second non-return-to-zero signal NRZ2 is required (Step S210). When the second non-return-to-zero signal NRZ2 is at low voltage level, the first counter 301 counts a first counting value DIFFCntH (DIFFCntH=DIFFCntH+1, as in Step S212), and then Step S204 is performed again. If the first non-return-to-zero signal NRZ1 is at the same voltage as the second non-return-to-zero signal NRZ2, then Step S204 keeps performing as well. However, when the first non-return-to-zero signal NRZ1 is at a low voltage level, the comparator 308 further determines whether the first non-return-to-zero signal NRZ1 has the same voltage level as the second non-return-to-zero signal NRZ2 (Step S214). At this moment, if the second non-return-to-zero signal NRZ2 is at high voltage level, the second counter 302 counts a second counting value DIFFCntL (DIFFCntL=DIFFCntL+1, as in Step S216), and then Step S204 is performed again. In another embodiment, when the first non-return-to-zero signal NRZ1 is at a low voltage level, and the second non-return-to-zero signal NRZ2 is at a high voltage level, the first counter 301 counts the first counting value DIFFCntH; conversely, when the first non-return-to-zero signal NRZ1 is at a high voltage level, and the second non-return-to-zero signal NRZ2 is at a low voltage level, the second counter 302 counts the second counting value DIFFCntL.

Once the time period timed by the timer 306 complies with the predetermined time period (Step S206), the calculating unit 304 sums the first counting value DIFFCntH and the second counting value DIFFCntL, and determines whether the sum of the first counting value DIFFCntH and the second counting value DIFFCntL is larger than a first predefined value LEVEL_B1. The calculating unit 304 also determines whether the second counting value DIFFCntL is larger than a product of the first counting value DIFFCntH and a second predefined value LEVEL_C1, or determines whether the first counting value DIFFCntH is larger than a product of the second counting value DIFFCntL and the second predefined value LEVEL_C1, (i.e., whether a ratio of the first counting value DIFFCntH and the second counting value DIFFCntL is larger than the second predefined value LEVEL_C1) (Step S218). In this embodiment, both the first predefined value LEVEL_B1 and the second predefined value LEVEL_C1 can be set to 8. If the result of Step S218 is false, it indicates that the pattern of the first non-return-to-zero signal NRZ1 from the ML detector 24 has fewer amount of differences with that of the second non-return-to-zero signal NRZ2 from the non-ML detector 26 in the predetermined time period. In this manner, the calculating unit 304 outputs a high-voltage-level selecting signal NRZSEL (Step S220), and Step S202 is performed again to make all the counters return to a value of zero. On the contrary, if the result of Step S218 is true, it indicates that the pattern of the first non-return-to-zero signal NRZ1 from the ML detector 24 has a sufficient number of differences with that of the second non-return-to-zero signal NRZ2 from the non-ML detector 26 in the predetermined time period. Accordingly, the calculating unit 304 outputs a low-voltage-level selecting signal NRZSEL (Step S222), and Step S202 is performed again to make all the counters 301, 302, 306 return to a value of zero.

Consequently, the selecting unit 28 outputs the first non-return-to-zero signal NRZ1 from the ML detector 24 as long as the selecting signal NRZSEL is at a high voltage level, otherwise outputs the second non-return-to-zero signal NRZ2 from the non-ML detector 26 as long as the selecting signal NRZSEL is at a low voltage level.

Please refer to FIG. 4 in conjunction with FIG. 2. FIG. 4 is a flowchart of the data recovery method according to another embodiment of the present invention. It is noted that the methods illustrated in FIGS. 3 and 4 are implemented by the decision unit 30 shown in FIG. 2 in more details, except the determination mechanism. As shown in FIG. 4, in the beginning, the first counter 301, the second counter 302, and the timer 306 returns to zero (Step S302) to get ready for counting an amount of differences between the first non-return-to-zero signal NRZ1 and the second non-return-to-zero signal NRZ2 in a predetermined time period. The timer 306 which can be implemented by a counter sequentially sums a counting value NRZCnt associated with a period cycle of the channel bit clock CBCLK (NRZCnt=NRZCnt+1, Step S304) until the counting value NRZcnt matches a predetermined value LEVEL_A (Step S306). As long as the counting value NRZcnt matches the predetermined value LEVEL_A, it indicates that the predetermined time period is up. In this embodiment, during the predetermined time period, the comparator 308 detects whether the first non-return-to-zero signal NRZ1 and the second non-return-to-zero signal NRZ2 are not at the same voltage level (Step S308). If both the first non-return-to-zero signal NRZ1 and the second non-return-to-zero signal NRZ2 are at the same voltage level, Step S304 is performed again. Otherwise, the comparator 308 further determines whether the first non-return-to-zero signal NRZ1 is at rising edge (Step S310) or falling edge. If the first non-return-to-zero signal NRZ1 is at rising edge, the first counter 301 counts a third counting value DIFFCntR (DIFFCntR=DIFFCntR+1, as in Step S312), and then Step S304 is performed again. If the first non-return-to-zero signal NRZ1 is at falling edge, the second counter 302 counts a fourth counting value DIFFCntF (DIFFCntF=DIFFCntF+1, as in Step S314), and then Step S304 is performed again.

Once the time period timed by the timer 306 complies with the predetermined time period (Step S306), the calculating unit 304 sums the third counting value DIFFCntR and the fourth counting value DIFFCntF, and determines whether the sum of the third counting value DIFFCntR and the fourth counting value DIFFCntF is larger than a third predefined value LEVEL_B2. The calculating unit 304 also determines whether the fourth counting value DIFFCntF is larger than a product of the third counting value DIFFCntR and a fourth predefined value LEVEL_C2, or determines whether the third counting value DIFFCntR is larger than a product of the fourth counting value DIFFCntF and the fourth predefined value LEVEL_C2 (i.e., whether a ratio of the third counting value DIFFCntR and the fourth counting value DIFFCntF is larger than the fourth predefined value LEVEL_C2) (Step S316). In this embodiment, both the third predefined value LEVEL_B2 and the fourth predefined value LEVEL_C2 can be set to 8. If the result of Step S316 is false, it indicates that the pattern of the first non-return-to-zero signal NRZ1 from the ML detector 24 has fewer differences with that of the second non-return-to-zero signal NRZ2 from the non-ML detector 26 in the predetermined time period. In this manner, the calculating unit 304 outputs a high-voltage-level selecting signal NRZSEL (Step S318), and Step S302 is performed again to make all the counters return to a value of zero. On the contrary, if the result of Step S316 is true, it indicates that the pattern of the first non-return-to-zero signal NRZ1 from the ML detector 24 has a sufficient number of differences with that of the second non-return-to-zero signal NRZ2 from the non-ML detector 26 in the predetermined time period. Accordingly, the calculating unit 304 outputs a low-voltage-level selecting signal NRZSEL (Step S320), and Step S302 is performed again to make all the counters 301, 302, 306 return to a value of zero.

Consequently, the selecting unit 28 outputs the first non-return-to-zero signal NRZ1 from the ML detector 24 as long as the selecting signal NRZSEL is at a high voltage level, otherwise outputs the second non-return-to-zero signal NRZ2 from the non-ML detector 26 as long as the selecting signal NRZSEL is at a low voltage level.

Please refer to FIG. 5, which is a functional block diagram of the decision unit 50 according to another embodiment of the present invention. For brevity, it is noted that elements in FIG. 5 have the same function as the ones illustrated in FIG. 2, therefore, are provided with the same item numbers as those used in FIG. 2. The decision unit 50 comprises a first counter 301, a second counter 302, a timer 306, a comparator 308, a signal-length calculator 502, a multiplexer 504, a threshold generator 506, a determining unit 508, and a delay unit 510.

Please refer to FIG. 5 in conjunction with FIG. 6, FIG. 6 illustrates a data recovery method flowchart according to another embodiment of the present invention. When the first non-return-to-zero signal NRZ1 from the ML detector 24 is fed into the signal-length calculator 502 via the multiplexer 504, the signal-length calculator 502 determines a length value NRZ1_length(n) associated with a length of the first non-return-to-zero signal NRZ1 (Step S402), and outputs the length value NRZ1_length(n) to the determining unit 508 and the delay unit 510. The delay unit 510 holds the length value NRZ1_length(n) for a short period of time (Step S404), and then outputs to the determining unit 508. At this moment, the determining unit 508 is used for outputting the selecting signal NRZSEL based on whether the length value NRZ1_length(n) and a previous length value NRZ1_length(n−1) from the delay unit 510 meets a criterion. In this embodiment, the determining unit 508 determines whether the length value NRZ1_length(n) is larger than a fifth predefined value Threshold_A, and determines whether the previous length value NRZ1_length(n−1) from the delay unit 510 is larger than a sixth predefined value Threshold_B (Step S406). Both the fifth predefined value Threshold_A, and the sixth predefined value Threshold_B are provided by the threshold generator 506 (Step S412). If the result of the Step S406 is true, the determining unit 508 outputs the selecting signal NRZSEL with a low voltage level (Step S408), otherwise, outputs the selecting signal NRZSEL with a high voltage level (Step S410). In this embodiment, depending on the user's demand, the fifth predefined value Threshold_A can be set to 4T or 5T, and the sixth predefined value Threshold_B can be set to 5T or 6T, where T indicates the period cycle of the channel bit clock (CBCLK). If the length value NRZ1_length(n) is larger than the fifth predefined value Threshold_A, (e.g. 6T), and the length value NRZ1_length(n−1) is larger than sixth predefined value Threshold_B (e.g. 5T), the determining unit 508 outputs the selecting signal NRZSEL with a low voltage level to the selecting unit 28, conversely, outputs the selecting signal NRZSEL with a high voltage level to the selecting unit 28. When receiving the selecting signal NRZSEL with a low voltage level, the selecting unit 28 alternatives the second non-return-to-zero signal NRZ2 from the non-ML detector 26 as its output NRZOUT. On the contrary, when receiving the selecting signal NRZSEL with a high voltage level, the selecting unit 28 switches the first non-return-to-zero signal NRZ1 from the ML detector 24 as its output NRZOUT.

The signal-length calculator 502 calculates a length value NRZ2_length(n) associated with a length of the second non-return-to-zero signal NRZ2 generated by the non-ML detector 26. Similarly, the determining unit 508 outputs a different voltage level of the selecting signal NRZSEL to the selecting unit 28 depending on a result of whether the length value NRZ2_length(n) is larger than a fifth predefined value Threshold_A, and whether the previous length value NRZ2_length(n−1) from the delay unit 510 is larger than a sixth predefined value Threshold_B. The selecting unit 28 selectively outputs the first non-return-to-zero signal NRZ1 from the ML detector 24 or the second non-return-to-zero signal NRZ2 from the non-ML detector 26 according to the selecting signal.

It is appreciated that, the fifth predefined value Threshold_A and the sixth predefined value Threshold_B can be set in advance, or both the predefined values Threshold_A and Threshold_B are provided by the threshold generator 506. In other words, the fifth predefined value Threshold_A and the sixth predefined value Threshold_B can be defined a constant value or dynamically adjusted.

Please refer to FIGS. 4-6. In order to dynamically generate the fifth predefined value Threshold_A and the sixth predefined value Threshold_B, the decision unit 50 further comprises the comparator 308, the first counter 301, the second counter 302, and the timer 306, which have the same functions as the ones illustrated in FIG. 2 and are provided with the same item numbers as those in FIG. 2. The timer 306 is used for timing a predetermined time period. In FIG. 4, the first counter 301 accumulates the third counting value DIFFCntR (Step S312) if the first non-return-to-zero signal NRZ1 is in a rising edge, and the voltage levels of the first and the second non-return-to-zero signals NRZ1, NRZ2 are not identical; conversely, the second counter 302 accumulates the fourth counting value DIFFCntF (Step S314) if the first non-return-to-zero signal NRZ1 is in a falling edge, and the voltage levels of the first and the second non-return-to-zero signals NRZ1, NRZ2 are not identical. As a result, for Step S412 in FIG. 6, the threshold generator 506 can adjust the fifth predefined value Threshold_A and the sixth predefined value Threshold_B based on the third counting value DIFFCntR from Step S312 and the fourth counting value DIFFCntF from Step S314. For example, given that an initial fifth predefined value Initial_TH_A is set to be 6T and an initial sixth predefined value Initial_TH_B is set to be 5T, when both criteria and a sum of the third counting value DIFFCntR, also the fourth counting DIFFCntF, is greater than a seventh predefined value LEVEL_B3, and the third counting value DIFFCntR does not equal to the fourth counting value DIFFCntF are satisfied, new fifth predefined value Threshold_A and sixth predefined value Threshold_B are generated as the following formula:

$$Threshold\_A=Initial\_TH\_A-K\times(DIFFCntR/DIFFCntF)$$

$$Threshold\_B=Initial\_TH\_B-K\times(DIFFCntF/DIFFCntR),$$

where K is a multiple factor.
Or, $$Threshold\_A=Initial\_TH\_A-K\times ABS(DIFFCntR-DIFFCntF)$$

$$Threshold\_B=Initial\_TH\_B-K\times ABS(DIFFCntR-DIFFCntF),$$

where ABS indicates a function of absolute value.

Besides using the third counting value DIFFCntR and the fourth counting value DIFFCntF to generate the fifth predefined value Threshold_A and the sixth predefined value Threshold_B, the first counting value DIFFCntH (from Step S212 in FIG. 2) and the second counting value DIFFCntL (from Step S216 in FIG. 2) are also allowed to generate the fifth predefined value Threshold_A and the sixth predefined value Threshold_B.

In contrast to prior art, the present invention utilizes a decision unit for determining an amount of differences between the patterns generated by the maximum-likelihood detector (e.g. Viterbi decoder), and the non-maximum-likelihood detector (e.g. data slicer) in a predetermined time period, and a selecting unit for switching the maximum-likelihood detector and the non-maximum-likelihood detector to perform data recovery based on the determined amount of differences. Consequently, properly switching the current maximum-likelihood detector and non-maximum-likelihood detector is a solution capable of improving data recovery efficiency without needing to design a new complex maximum-likelihood detector.

Although the present invention has been explained by the embodiments shown in the drawings described above, it should be understood to the ordinary skilled person in the art that the invention is not limited to the embodiments, but rather various changes or modifications thereof are possible without departing from the spirit of the invention. Accordingly, the scope of the invention shall be determined only by the appended claims and their equivalents.

BRIEF DESCRIPTION OF THE DRAWINGS

FIG. 6 illustrates a flowchart of a data recovery method according to another embodiment of the present invention.

Figure 1:
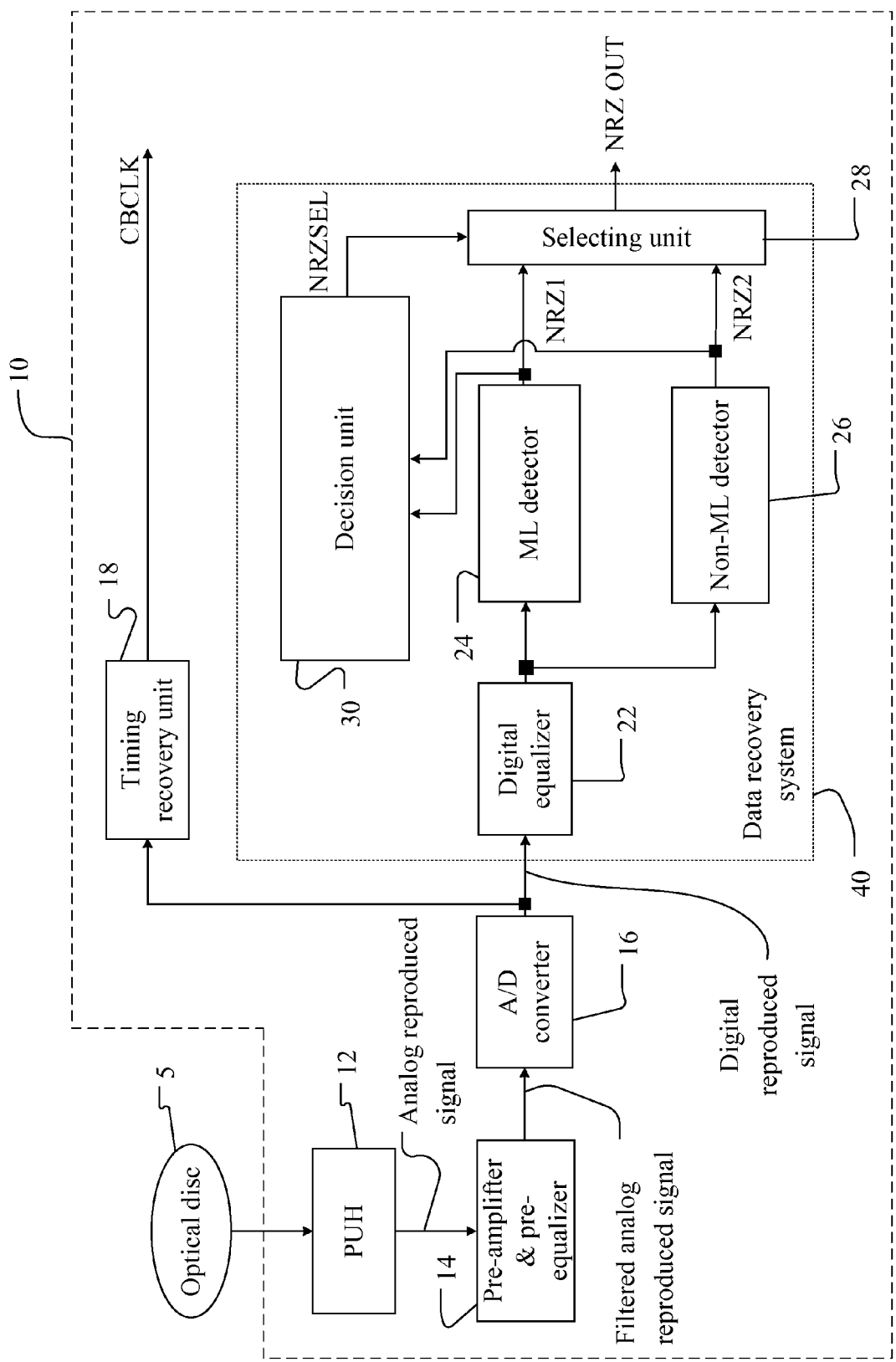
FIG. 1 is a functional block diagram of a preferred embodiment of a data recovery system according to the present invention.
Figure 2:
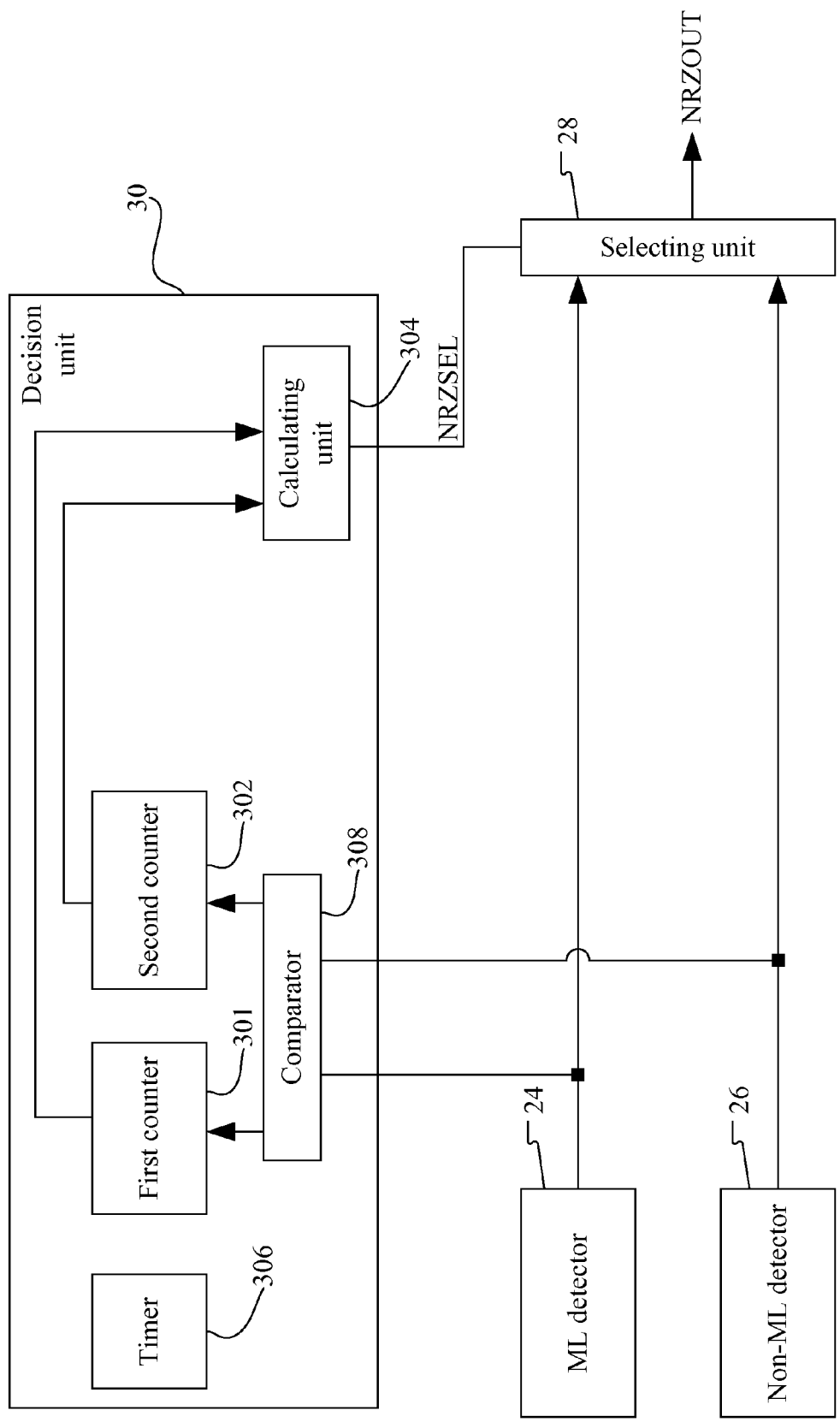
FIG. 2 is a functional block diagram of a preferred embodiment of the decision unit depicted in FIG. 1.
Figure 3:
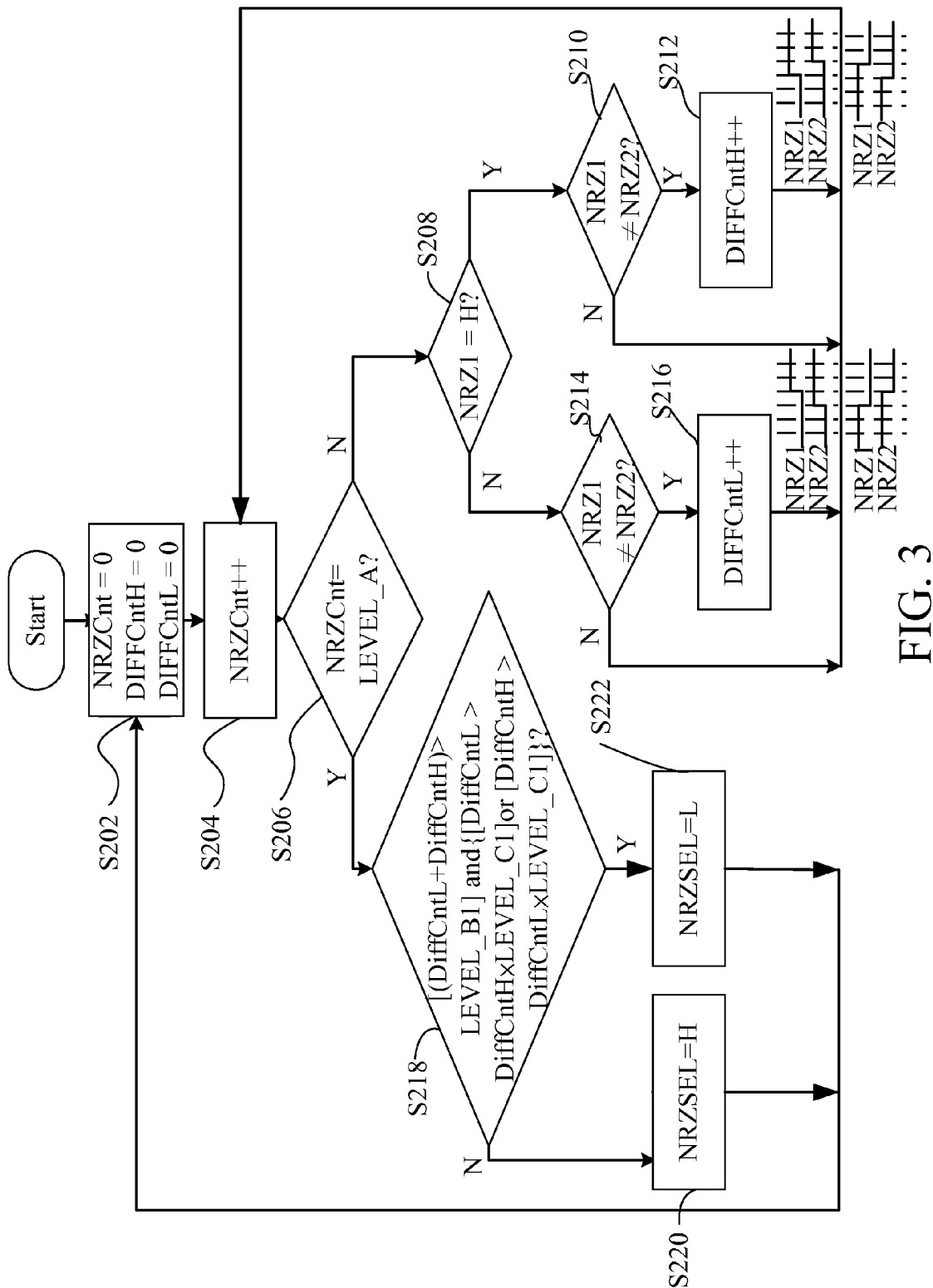
FIG. 3 is a flowchart of a preferred embodiment method incorporating with the decision unit depicted in FIG. 2.
Figure 4:
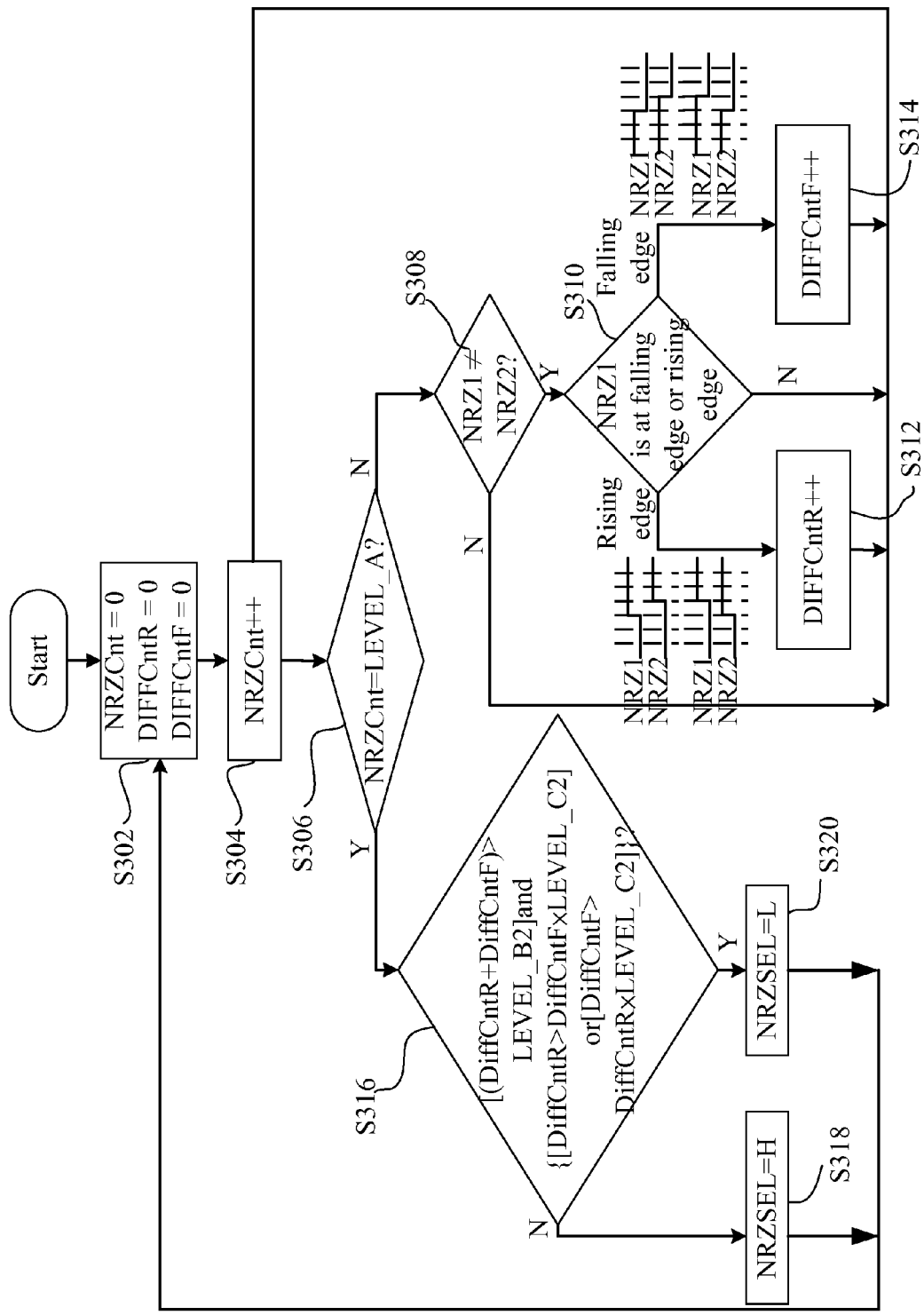
FIG. 4 is a flowchart of the data recovery method according to another embodiment of the present invention.
Figure 5:
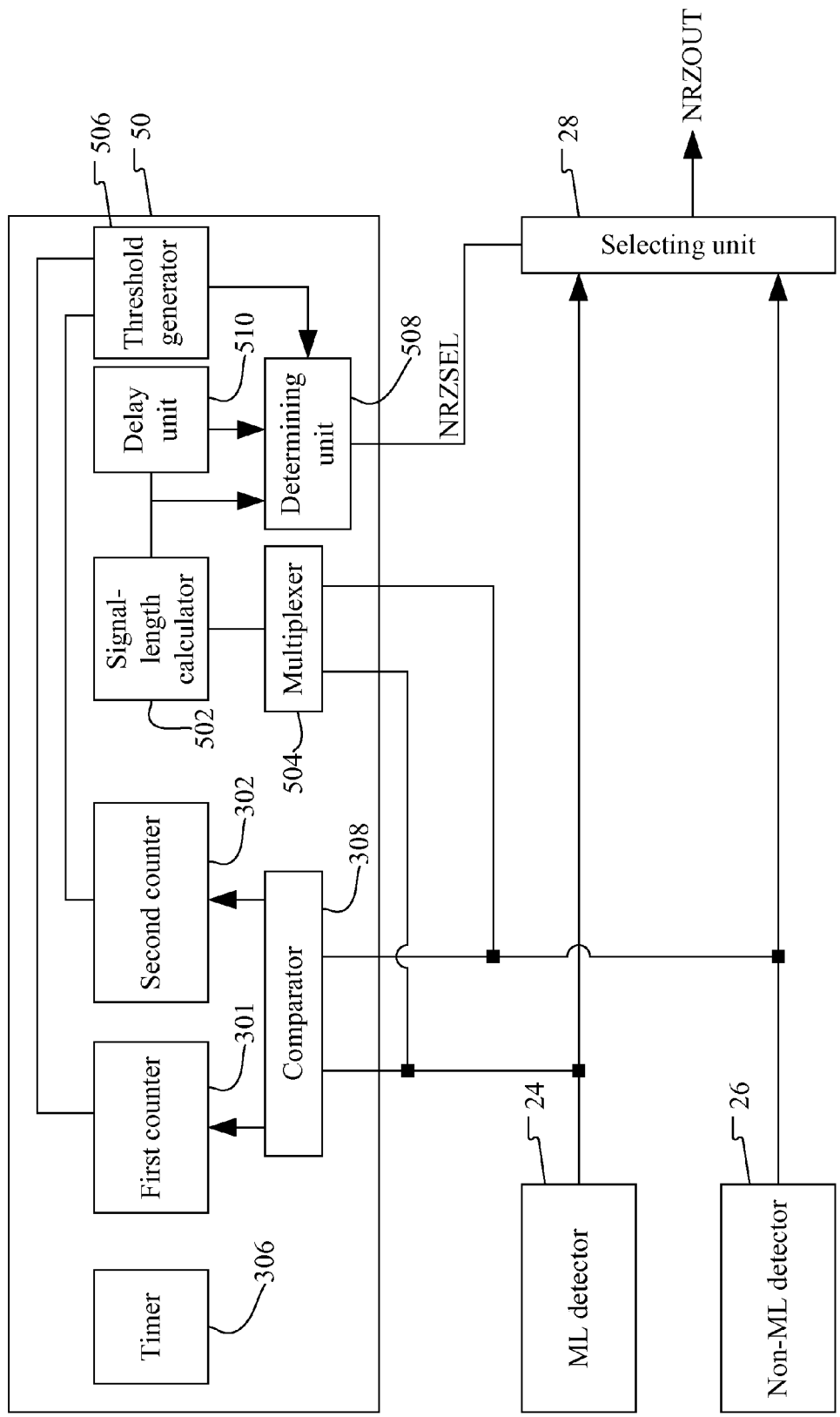
FIG. 5 is a functional block diagram of the decision unit according to another embodiment of the present invention.

What is claimed is:

1. A data recovery system comprising:
   a maximum-likelihood detector for transforming a digital signal into a first binary signal;
   a non-maximum likelihood detector for transforming the digital signal into a second binary signal;
   a signal-length calculator for calculating a length of the first binary signal and a length of one previous to the first binary signal;
   a determining unit for generating a selecting signal when the length of the first binary signal and the length of one previous to the first binary signal meet a criterion; and
   a selecting unit, coupled to the maximum likelihood detector and the non-maximum likelihood detector, for selectively outputting the first binary signal or the second binary signal based on the selecting signal.

2. The data recovery system of claim 1, wherein the criterion indicates the length of the first binary signal is larger than a first predefined value, and the length of the one previous to the first binary signal is larger than a second predefined value.

3. The data recovery system of claim 2, wherein data recovery system further comprises:
   a timer for timing a predetermined time period;
   a first counter, in the predetermined time period, for counting a first counting value indicating an amount of the differences between the first binary signal at a first logical level and the second binary signal at a second logical level; and
   a second counter, in the predetermined time period, for counting a second counting value indicating an amount of the differences between the first binary signal at the second logical level and the second binary signal at the first logical level; and
   a threshold generator for adjusting the first predefined value and the second predefined value based on the first counting value and the second counting value when a sum of the first counting value and the second counting value is larger than a third predefined value, and when the first counting value does not equal to the second counting value.

4. The data recovery system of claim 2, wherein data recovery system further comprises:
   a timer for timing a predetermined time period;
   a first counter, in the predetermined time period, for counting a third counting value indicating an amount of the differences, when a logical level of the first binary signal and a logical level of the second binary signal are not identical when the first binary signal is in a rising edge;
   a second counter, in the predetermined time period, for counting a fourth counting value indicating an amount of the differences, when the logical level of the first binary signal and the logical level of the second binary signal are not identical when the first binary signal is in a falling edge; and
   a threshold generator for adjusting the first predefined value and the second predefined value based on the third counting value and the fourth counting value when a sum of the third counting value and the fourth counting value is larger than a third predefined value, and when the third counting value do not equal to the fourth counting value.

5. The data recovery system of claim 1, wherein the first binary and the second binary signals are selected from a group consisting of a non-return-to-zero (NRZ) signal and a non-return to zero inverted (NRZI) signal.

6. The data recovery system of claim 1, wherein the maximum-likelihood detector is a Viterbi decoder.

7. The data recovery system of claim 1, wherein the non-maximum likelihood detector is a data slicer.

8. A data recovery method comprising:
   receiving a digital signal;
   transforming the digital signal into a first binary signal by using maximum-likelihood logic;
   transforming the digital signal into a second binary signal by using non-maximum likelihood logic;
   calculating a length of the first binary signal and a length of one previous to the first binary signal;
   generating a selecting signal when the length of the first binary signal and the length of one previous to the first binary signal meet a criterion; and
   selectively outputting the first binary signal or the second binary signal based on the selecting signal.

9. The data recovery method of claim 8, wherein the criterion indicates the length of the first binary signal is larger than a first predefined value, and the length of one previous to the first binary signal is larger than a second predefined value.

10. The data recovery method of claim 9, further comprising:
    counting a first counting value indicating an amount of the differences between the first binary signal at a first logical level and the second binary signal at a second logical level in a predetermined time period; and
    counting a second counting value indicating an amount of the differences between the first binary signal at the second logical level and the second binary signal at the first logical level in the predetermined time period; and
    adjusting the first predefined value and the second predefined value based on the first counting value and the second counting value, when a sum of the first counting value and the second counting value is larger than a third predefined value, and when the first counting value does not equal to the second counting value.

11. The data recovery method of claim 10, wherein the first logical level is a high voltage level, and the second logical level is a low voltage level.

12. The data recovery method of claim 10, wherein the first logical level is a low voltage level, and the second logical level is a high voltage level.

13. The data recovery method of claim 9, further comprising:
counting a third counting value indicating an amount of the differences, when a logical level of the first binary signal and a logical level of the second binary signal are not identical when the first binary signal is in a rising edge in a predetermined time period;
counting a fourth counting value indicating an amount of the differences, when the logical level of the first binary signal and the logical level of the second binary signal are not identical when the first binary signal is in a falling edge in the predetermined time period; and
adjusting the first predefined value and the second predefined value based on the third counting value and the fourth counting value, when a sum of the third counting value and the fourth counting value is larger than a third predefined value, and when the third counting value do not equal to the fourth counting value.

14. The data recovery method of claim 8, wherein the first binary and the second binary signals are selected from a group consisting of a non-return-to-zero (NRZ) signal and a non-return to zero inverted (NRZI) signal.

* * * * *